United States Patent [19]

Iwamura

[11] Patent Number: 5,272,062

[45] Date of Patent: Dec. 21, 1993

[54] MEASUREMENT OF CATALASE ACTIVITY

[76] Inventor: Junichi Iwamura, 621-1, Takaida, Kashiwara-shi, Osaka-fu, Japan

[21] Appl. No.: 854,284

[22] Filed: Mar. 19, 1992

[30] Foreign Application Priority Data

Mar. 22, 1991 [JP] Japan .................................. 3-83520

[51] Int. Cl.$^5$ .......................... C12Q 1/30; C12Q 1/32; C12N 9/08
[52] U.S. Cl. ...................................... 435/27; 435/26; 435/192; 435/810
[58] Field of Search .................... 435/27, 26, 192, 810

[56] References Cited

U.S. PATENT DOCUMENTS 4,202,938  5/1980  Haeckel ................................ 435/10
4,855,228  8/1989  Charlton .............................. 435/28

FOREIGN PATENT DOCUMENTS 67499  4/1986  Japan .

OTHER PUBLICATIONS

Van Lente, F., Coupled-Enzyme Determination of Catalase Activity . . . , Clinical Chemistry 36 (7) 1339-1343 (1990).
Yasmineh, W. G., Determination of Serum Catalase Activity . . . , Clinical Biochemistry 25 pp. 21-27, Feb. 1992.
Chemical Abstracts, vol. 107, No. 1, Jul. 6, 1987, Columbus, Ohio, USA N. Hughes, "A method for direct measurement of catalase activity", p. 601 Abstract No. 6497s and J. Coll. Sci. Teach. 1987, 16(6), 541-543.
Chemical Abstracts, vol. 108, No. 17, Apr. 25, 1988, Columbus, Ohio, USA M. A. Korolyuk et al., "A method for measuring catalase activity", p. 319 Abstract No. 145883y and Lab. Delo 1988, (1), 16-19.
Chemical Abstracts, vol. 110, No. 25, Jun. 19, 1989, Columbus, Ohio, USA D. Boismenu et al., "Catalase activity measurement with the disk flotation method", p. 260, Abstract No. 227507j and Anal. Biochem. 1989, 178(2), 404-407.
H. J. Bergmeyer "Methods of Enzymatic Analysis", 3rd Edition, vol. III; Enzymes 1; Oxidoreductases, Transferases, 1983, Verlag Chemie, Weinheim, pp. 273-286, p.276, table 1.
J. Biol. Chem. vol. 195, 133-140, 1952.
Rinsho Kagaku vol. 15, No. 1 (1986) 20-27.
Rinsho Kagaku vol. 15, No. 3 (1986) 152-160.
Rinsho Byori (Japanese Journal of Clinical Pathologh) vol. 24, No. 1, 68-72.
Rinshokensa (Clinical Analysis) vol. 35, No. 13, 1347-1350 Dec. 15, 1991.
Igaku To Seibutsugaku, 1971, 82(1), 33-38.
Rinsho Byori, 1974, 22(11), 807-810.
Clin. Chem. 30/6, 843-846 (1984).
Clin. Chem. vol. 28, No. 9, 1982.
Clin. Biochem. vol. 25, 21-27 1992.
Methods of Enzymatic Analysis vol. 2, 673-684 (1974).
Acta Chem. Scan. 1 (1947) 236-267.
Medical Journal of Osaka University vol. 12, No. 1-2, Jul. 1961.
Clin. Chem. vol. 29, No. 4 1983, 741-743.
Digestive Diseases, vol. 18, No. 12 (Dec. 1973), 1035-1041.
Acta Biol. Hungarica 38(2), 279-285 (1987).
Analytical Biochem. 184, 193-199 (1990).
Proc. Soc. Ex. Biol. Med. vol. 84, 74-79, 1953.
Agr. Biol. Chem. 38(6), 1213-1220, 1974.
The Journal of Biochem. vol. 49, No. 6, 1961, 707-712.
Pancreas-Communications Libres, 112c 1972.

Primary Examiner—Michael G. Wityshyn
Assistant Examiner—Ralph Gitomer

[57] ABSTRACT

A method of measurement of catalase activity in a sample suspected of containing such activity which comprises treating said sample with a peroxide, an alcohol, nicotinamide adenine dinucleotide (NAD) and an aldehyde dehydrogenase, thereby producing an aldehyde corresponding to said alcohol and converting NAD to its reduced form (NADH), measuring absorption of radiation having a wave length at the characteristic absorption band of NADH in relation to said activity.

3 Claims, 2 Drawing Sheets

MEASUREMENT OF CATALASE ACTIVITY

BACKGROUND OF THE INVENTION

1. Field of the Invention

The present invention relates to a method of measurement of catalase and a kit useful in such measurement.

2. Background Information

Catalase is a well known enzyme which effects detoxication of oxygen-toxicity. Particularly, great importance has been attached to the measurement of activity of this enzyme since the serum catalase activity rises in patients of acute or chronic hepatitis, hepatic carcinoma, pyelonephritis and particularly acute pancreatitis (Rinshobyori, 24, 68, 1975) and therefore the measurement of such activity is very significant.

Various methods for measuring catalase activity have been reported up to date, such as a method in which decrease in hydrogen peroxide is measured by decrease in ultraviolet absorption of hydrogen peroxide (J. Biol. Chem., 195, 133, 1952), a method in which an amount of oxygen produced by decomposition of hydrogen peroxide is measured by an oxygen electrode (Rinshobyori, 22, 807, 1973), a method in which heat of formation is measured (Proc. Soc. Exp. Biol. Med., 84. 74, 1953), a method in which an amount of precipitate is measured (J. Biochem., Tokyo, 49, 707, 1961), a method in which an amount of residual hydrogen peroxide after reaction is measured (Acta Chem. Scand., 1, 236, 1947) and a method in which titanium sulfate is complexed and absorption of the formed complex is measured (Z. physiol. Chem., 335, 146, 1964). All the known method , however, are not easy to be used in the clinical test field in which rapidity and accuracy are regarded as particularly important because these methods either use special apparatus, or strong acid, or involve many problems in operability and accuracy.

SUMMARY OF THE INVENTION

The present invention is aimed to solve such problems.

In the method for measuring catalase activity according to the present invention, a peroxide is reacted as the substrate for catalase in the presence of an alcohol to produce an aldehyde, the amount of which is converted to the amount of nicotinamide adenine dinucleotide in reduced form (NADH) through the action of an aldehyde dehydrogenase and increase in the amount of NADH is determined by the change of absorption at the characteristic absorption region of NADH and correlated to the catalase activity.

Thus, the present invention provides 1) a method of measurement of catalase activity in a sample suspected of containing such activity which comprises treating said sample with a peroxide, an alcohol, nicotinamide adenine dinucleotide (NAD) and an aldehyde dehydrogenase, thereby producing an aldehyde corresponding to said alcohol and converting NAD to its reduced form (NADH), measuring absorption of radiation having a wave length at the characteristic absorption band of NADH in relation to said activity.

2) a kit for measuring catalase activity comprising
   a) an alcohol,
   b) NAD,
   c) an aldehyde dehydrogenase, and
   d) hydrogen peroxide.

3) a kit for measuring catalase activity comprising
   (a) a buffer solution containing an alcohol, NAD and an aldehyde dehydrogenase, and
   b) a solution containing hydrogen peroxide.

BRIEF DESCRIPTION OF DRAWINGS

In the accompanied drawings.

DETAILED DESCRIPTION OF THE INVENTION

Figure 1:
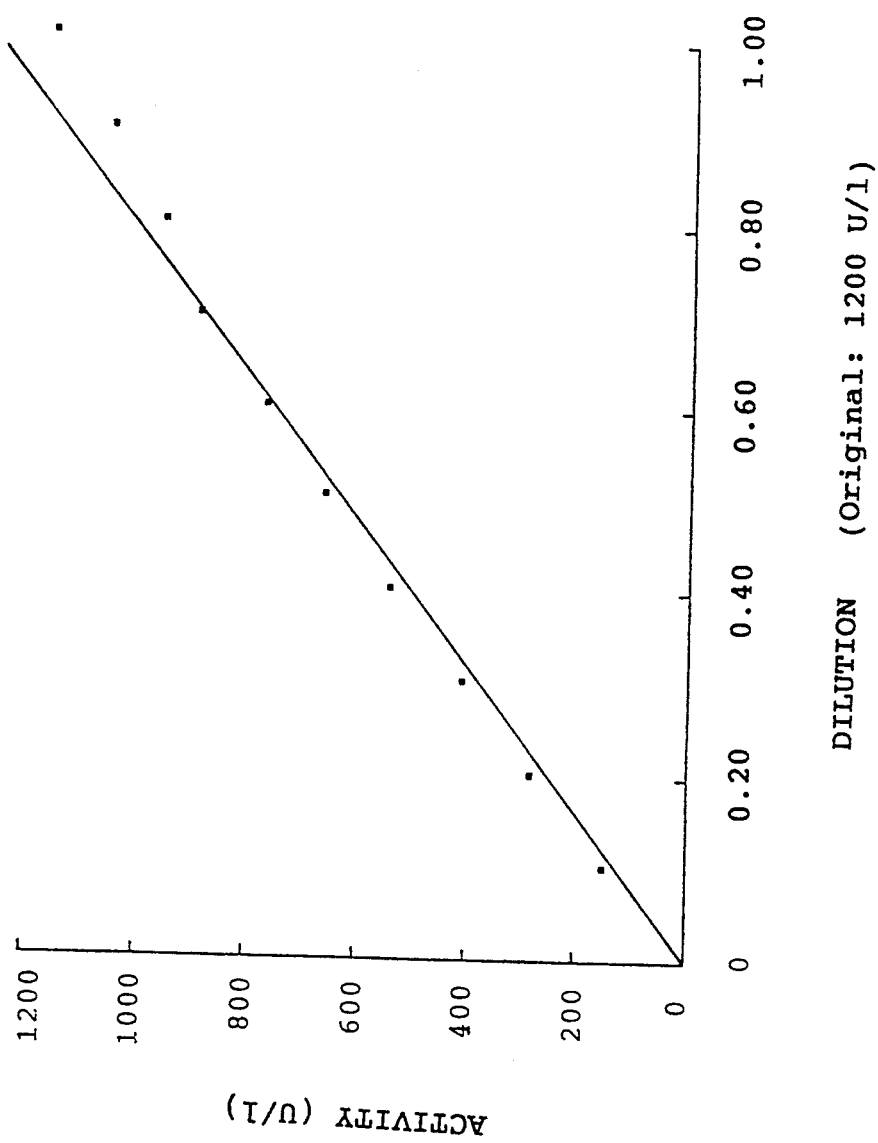
FIG. 1 is a graphic representation of catalase activity measured according to the present invention showing the linearity of data, and FIG. 2 represent relationship between the activity measured by the method according to the present invention and the activity measured by the known method (titanium method).

The reaction which occurs in the present invention is summarized as follows:

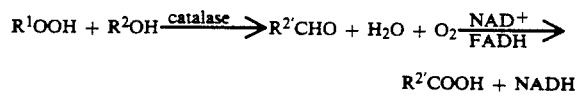

$$R^{2'}COOH + NADH$$

wherein $R^1$ is a residual group of peroxide when the hydroperoxide group is removed, $R^2$ is a residual group of alcohol when the hydroxy group is removed, $R^{2'}$ is a residual group of $R^2$ when a carbon atom is removed, and FADH is formaldehyde dehydrogenase.

According to a preferred embodiment of the present invention, a buffer solution having a pH of 6-9 and containing a peroxide, NAD and an alcohol is used as the assay reagent. The said assay reagent is combined with a sample solution to allow to take place the above reaction thereby producing NADH. Then ultraviolet absorption at a wave length within the characteristic absorption region of NADH is measured and related to catalase activity.

The sample is typically obtained from biological source such as animal and plant. Examples of the sample include blood, blood plasma, serum, tissue homogenate, tissue fluid, tear, lymph, cerebrospinal fluid, saliva and urine. Preferred samples are serum and tissue related samples.

Examples of the peroxide include hydrogen peroxide and organic peroxide such as lower (i.e. $C_{1-6}$) alkyl hydroperoxide (for example, methyl hydroperoxide, ethyl hydroperoxide, etc.) and aryl hydroperoxide, preferably monocyclic aryl or substituted or unsubstituted phenyl hydroperoxide (for example, phenyl hydroperoxide, cumenyl hydroperoxide, etc.) and other peroxide such as, cumene peroxide.

Examples of the alcohol include lower (i.e. $C_{1-6}$) alkanol (for example, methanol, ethanol, butanol, etc.) and aryl(lower)alkyl alcohol (for example, benzyl alcohol, etc.).

Preferred examples of the aldehyde dehydrogenase include formaldehyde dehydrogenase, acetaldehyde dehydrogenase, etc.

A specific example of the assay reagent may be a buffer solution containing 90-540 m mole/l hydrogen peroxide, 1-7 mole/l methanol, 0.01-3 m mole/l NAD and 10-1000 U/l formaldehyde dehydrogenase and has a pH of 6-9. The buffer may be a phosphate buffer, Good's buffer, Tris buffer, etc.

The determination of catalase according to the present invention may either be conducted by the end-point method wherein the reaction is quenched at the endpoint, or by the rate-assay method wherein change in absorption per unit time is measured.

The method for measuring catalase activity according to the present invention can easily be applied to general autoanalyzers for laboratory or clinical analysis.

A more complete understanding of the present invention will be obtained by reference to the following non-limiting Examples.

EXAMPLE 1

(1) Composition of the Assay Reagents

1) Reagent 1

A phosphate buffer solution of pH 7.8 containing the following components:

| Methanol | 2.5 mole/l |
|---|---|
| Formaldehyde dehydrogenase | 850 U/l |
| NAD | 0.75 m mole/l |

2) Reagent 2

A phosphate buffer solution of pH 7.8 containing 270 m mole/l hydrogen peroxide.

(2) Assay Procedure

Add 0.1 ml of a sample for measuring catalase activity to 3 ml of Reagent 1 and preincubate the mixture at 37° C. for 1 to 5 minutes. Then, add 0.1 ml of Reagent 2 to the mixture and measure change in absorption (or transparency) at the characteristic absorption band of NADH from 0.1 to 5 minutes after the addition of Reagent 2.

A solution containing known amounts of catalase can be used as the sample solution in order to relate experimentally obtained values of absorption to catalase activity. Catalase activity of a test sample containing unknown amount of activity can be determined by comparing the value of absorption obtained by the test sample with the values obtained by the samples with known amount of catalase. Alternatively, the molecular absorption of NADH can be used for the calculation of the activity.

FIG. 1 shows a calibration curve (plotting) obtained from standard catalase solutions containing known amount of activity (original solution: 1200 U/l and dilutions), indicating that the curve is linear and thus the assay can be used up to 1200 U/l of catalase activity.

EXAMPLE 2

The method of Example 1 applied to human serum samples is compared with the generally accepted titanium method.

Figure 2:
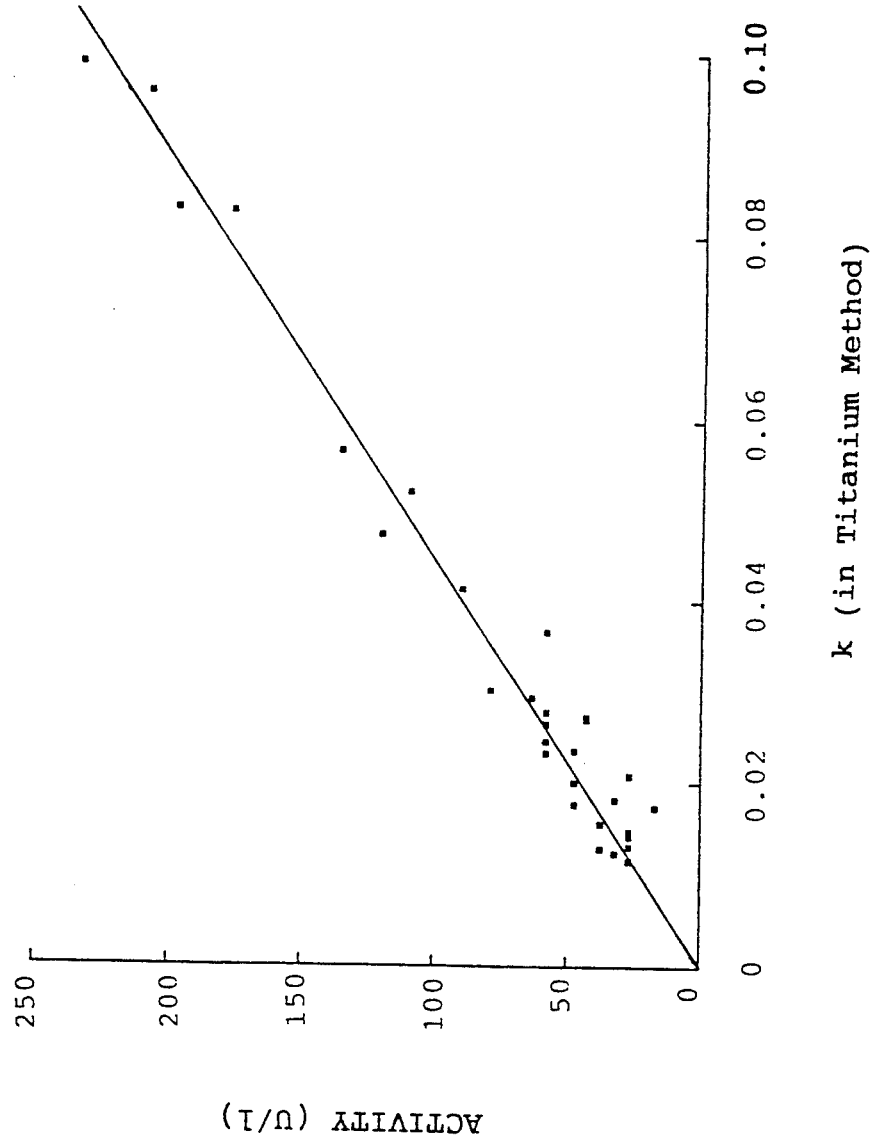

FIG. 2 shows the good correlation of the two method, wherein correlation coefficient $\gamma$ is 0.9846, $p < 0.01\%$ and n is 30 (including 25 normal sample).

From the above description, it can be clearly understood that the method according to the present invention is very simple, can be easily worked and has a good correlation with the conventional method. Furthermore, the method of the invention becomes accustomed to the operator of laboratory analysis in which the measurement of catalase is meaningful because the method uses absorption of NADH which is very familiar in the field of such analysis.

In addition, the method can be carried out with only two reagents, at 37° C., without using costly apparatus or corrosive reagents.

What is claimed is:

1. A method of measurement of catalase activity in a fluid sample suspected of containing such activity, said fluid sample selected from the group consisting of blood plasma, serum, tissue homogenate, tissue fluid, lymph fluid and cerebrospinal fluid, which method comprises treating said fluid sample with a peroxide, an alcohol, nicotinamide adenine dinucleotide (NAD) and an aldehyde dehydrogenase, said peroxide selected from the group consisting of hydrogen peroxide and an organic peroxide, said peroxide being capable of acting as a substrate of said catalase and oxidizing said alcohol to a corresponding aldehyde and being present in molar excess, and said alcohol being capable of acting as a substrate of said catalase thereby producing said aldehyde and converting NAD to its reduced form NADH, and measuring absorption of radiation having a wave length at the characteristic absorption band of NADH in relation to said activity.

2. A method according to claim 1, wherein the peroxide is a lower alkyl hydroperoxide.

3. A method according to claim 1, wherein the alcohol is selected from the group consisting of a lower alkanol and an aryl alkanol.

* * * * *

UNITED STATES PATENT AND TRADEMARK OFFICE
CERTIFICATE OF CORRECTION

PATENT NO. : 5,272,062
DATED : December 21, 1993
INVENTOR(S) : JUNICHI IWAMURA It is certified that error appears in the above-identified patent and that said Letters Patent is hereby corrected as shown below:

Col. 4, claim 3, line 46, of the claim, "aryl alkanol" should read
--aryl(lower)alkanol--.

Signed and Sealed this

Twenty-eighth Day of June, 1994

Attest:

BRUCE LEHMAN

Attesting Officer

Commissioner of Patents and Trademarks